United States Patent [19] [11] 4,025,392
Dougherty [45] May 24, 1977

[54] CHROMOGENIC SUBSTRATE FOR DETERMINATION OF AMYLASE ACTIVITY

[75] Inventor: Therese Marie Dougherty, Lansdale, Pa.

[73] Assignee: The United States of America as represented by the Secretary of Agriculture, Washington, D.C.

[22] Filed: Apr. 14, 1976

[21] Appl. No.: 676,949

[52] U.S. Cl. .................. 195/99; 195/101; 195/103.5 S
[51] Int. Cl.$^2$ .................. G01N 33/00; G01N 31/14
[58] Field of Search ............. 195/103.5 R, 101, 99; 536/102

[56] References Cited

UNITED STATES PATENTS 3,679,661  7/1972  Babson .................. 195/103.5 R

OTHER PUBLICATIONS

Ewen, "Synthesis of Cibachron Blue F3GA–Amylose with Increased Sensitivity for Determination of Amylase Activity" Clinica Chemica Acta., 47, (1973) pp. 233–248.

Klein et al., Clinical Chem. vol. 16, No. 1, (1970) pp. 32–38.

Lang, "Biochemists' Handbook", D. Van Nostrand Co., Inc., Princeton, N.J. 1961 p. 232.

Primary Examiner—Alvin E. Tanenholtz
Assistant Examiner—C. A. Fan
Attorney, Agent, or Firm—M. Howard Silverstein; David G. McConnell; W. E. Scott

[57] ABSTRACT

An improved chromogenic substrate for α-amylase assays is synthesized by reacting amylose with Cibachron Blue F3GA, sodium sulfate and trisodium phosphate and incubating the resultant dyed amylose substrate with a buffer containing calcium chloride. The new substrate is more sensitive than commercially available chromogenic substrates in determining the α-amylase activity of the enzymes of sweet potato, tobacco, and human saliva.

2 Claims, No Drawings

CHROMOGENIC SUBSTRATE FOR DETERMINATION OF AMYLASE ACTIVITY

BACKGROUND OF THE INVENTION

1. Field of the Invention

This invention relates to an improved dyed amylose for α-amylase assays and more particularly to an improved dyed amylose for the analysis of plant α-amylases.

2. Description of the Prior Art

Chromogenic substrates for the determination of amylase activity are not new to the art. Generally, they are been prepared by reacting amylose with Cibachron Blue F3GA (a monochlorotriazine dye with aminobenzene sulfonate on one carbon atom and amino anthoquinone sulfonic acid on a second carbon atom and has a molecular weight of 773.5), sodium sulfate and trisodium phosphate. Although the order of introducing the reagents varies depending on the person preparing the substrate, a widely used procedure is described by Klein et al, Anal. Biochem. 31, 412-425, 1969. An aqueous suspension of amylose is warmed and treated with an aqueous solution of Cibachron Blue F3GA. Sodium sulfate is added gradually followed by a warm aqueous solution of trisodium phosphate. After heating and stirring the mixture for about 75 minutes, the dyed amylose is allowed to settle and the supernatant fluid is removed. The residue is resuspended in water with vigorous stirring, allowed to settle, and the supernatant fluid removed. The residue is then washed with methanol, air-dried, and milled to 60-200 mesh. The dyed-amylose substrate was then used at a level of 200 mg/assay to determine amylose activity in human serum and saliva, crystalline hog pancreatic α-amylase, and fungal amyloglucosidase. Ewen, Clinica Chimica Acta 47, 233-245, 1973, prepared a dyed amylose substrate using the same reagents that Klein et al used but varied the order in which the reagents where combined. Although a tenfold increase in sensitivity was claimed for this preparation, each assay still required the use of 200 mg of substrate for the determination of amylose activity in human serum and in 24 hour urine specimens.

Although, as described above, chromogenic substrates have been widely used for α-amylase assays in the medical and clinical fields, the commerically available chromogenic substrates have not been very suitable for analysis of plant α-amylases. Dyed amylopectin has been used to determine α-amylases in sweet potatoes (J. Food Sci. 38, 548, 1973). However, at 40° C incubation, extrapolation to 'zero' enzyme concentration gave an absorbance of about 0.03 units (625 nm), and the linear portion at 40° C extended only to 0.225 absorbance units. At 60° C linearity was observed only up to 0.45 (595 nm).

SUMMARY OF THE INVENTION

An object of this invention is provide an improved chromogenic substrate for the determination of amylase activity.

Another object of this invention is to provide a chromogenic substrate that is suitable for the analysis of plant α-amylase.

A further object is to provide a highly sensitive chromogenic substrate for use in assaying very dilute enzyme extracts.

A still further object is to provide a precise, simple, rapid method for determing α-amylase.

Still another object is to provide a method of preparing an improved chromogenic substrate for the determination of α-amylase activity.

According to this invention the above objects are accomplished by an improved chromogenic substrate for use in determining amylase activity prepared by reacting amylose with Cibachron Blue F3GA, $Na_2SO_4$ and $Na_3PO_4$ to obtain a dyed amylose substrate and then incubating the dyed amylose substrate with a buffer containing calcium chloride.

DETAILED DESCRIPTION OF THE INVENTION

In view of the fact that the standard procedures for determining α-amylase in plants are time consuming, that chromogenic substrates are reportedly nonreactive with β-amylase, and that assay procedures using chromogenic substrates are simple and rapid, the present invention provides a much needed product and process for determining enzyme activity. For example, in the production of sweet potato flakes where processing conditions are altered relative to the α-amylase activity of the roots, the improved substrate of this invention provides a much needed means of rapidly determining the α-amylase activity.

The initial steps in the preparation of the improved substrate of this invention are based on the procedure of Klein et al, supra, with modifications in the amount of reactants and reaction temperature. The substrate obtained by the modified procedure of Klein et al was then incubated in phosphate buffer containing calcium chloride, centrifuged, washed, and freeze dried.

More specifically, the following is a preferred process for preparing the chromogenic substrate of this invention.

Cibachron Blue F3GA (12.5g.) in 1.25 liters of water at 60° C was added to a mixture of 125 g. amylose in 1.25 liters of water at 60° C. Sodium sulfate, 370 g., was gradually added followed by a solution of 12.5 g. trisodium phosphate in 180 m. of water and the aqueous mixture heated at about 60° C and stirred slowly for about an additional 75 minutes. The dyed amylose product was first water washed until the supernatant wash had a pH value of 6.0–6.5, then methanol washed and air dried. The air dried product was then shaken with about 1.2 liters of water for about 3 3/4 hours while being warmed at about 50° C. A water bath is suitable for this purpose. The aqueous mixture was centrifuged and the supernatant decanted. Lumpy material was disintegrated and the small particles incubated at about 44°C for about 1 1/2 hours in about 2.8 liters of 0.04M phosphate buffer (pH 6.2) containing 0.001M calcium chloride. The incubated product was then centrifuged, washed with water until the washings were practically colorless, and then freeze dried. Substrates made by this process were found to be very stable at room temperature (20–25°C). Since the substrates of this invention were not known prior to this invention, their stability at room temperature has been confirmed only for one and one-half years. However, there is no reason to believe that they will not be stable for many years.

It is hypothesized that in the preparation process the reaction induces a change or changes in the conformation of the substrate which provides energetically favorable binding at the enzyme active sites. However, the exact nature of the changes and of the composition of the new substrate is not yet known.

Although the process described above is the preferred one for making the substrate of this invention, some of the conditions of the reaction can be varied without adversely affecting the results. For example, the ratio of Cibachron Blue to amylose may be varied between 1:8 and 1:12; the temperature of reaction may be varied between 60 and 80° C, and the time of reaction may be varied depending on the temperature and other reaction conditions; and time and temperature at which the air dried- dyed amylose was shaken were merely arbitrary conditions and not considered critical to the success of the invention.

In general, α-amylase assays were made by incubating the substrate of this invention with an enzyme extract from a plant, an animal, or a human source in phosphate buffer containing $CaCl_2$.

More specifically, 70 mg. of the substrate of this invention was incubated with 0.2 ml sweet potato extract in 2.3 ml of 0.04M phosphate buffer (pH 6.0) containing 0.001M $CaCl_2$ at 40±0.2° C in a process similar to that described by Klein et al, Clin. Chem. 16, 32, 1970. The reaction was terminated by addition of 4.5 ml of 1.8% trichloroacetic acid. About 0.1 gm of a diatomaceous earth adsorbent (Celite) was added prior to centrifugation. Absorbance of the supernatant was measured against a blank or control at 625 nm. It was found that reaction of 20 mg of the substrate with enzyme in 1.0 ml incubation volume and 4.2 ml final volume was linear up to an absorbance of 0.35 (625 nm); hence, only 20 mg of the substrate is needed with dilute enzyme systems. It was also found that the color of the supernatant after removal from the substrate was very stable.

Tobacco enzyme was incubated with the substrate of this invention in phosphate buffer (pH 6.25) containing 0.001M $CaCl_2$ at 37° C. Acetate buffer, 0.1M, at pH 3.5 was effective in terminating the reaction.

Human saliva in 0.9% NaCl was reacted with the substrate of this invention at 37° C in phosphate buffer (pH 7.0) containing 0.02 M NaCl, and the reaction terminated with acetate buffer.

Sample absorbance readings from the assays were converted to dye units by reference to a calibration curve constructed as described by Ewen, supra. One unit of enzyme activity is defined as the amount of enzyme which results in liberation of 0.01 micromole of dye per minute under the conditions defined for assay.

In order to compare the efficacy of the subsrate of this invention with known substrates, α-amylase was determined in tobacco enzyme, sweet potato enzyme and salivary enzyme using a commercially available chromogenic substrate, Amylochrome, which is a Cibachron Blue F3GA — amylose. Preparation of Amylochrome and its probable structure are described by Klein et al (Anal. Biochem. and Clin. Chem., supra). Tobacco α-amylase was determined using water washed Amylochrome following the procedure described above for the reaction of the new dyed amylose with tobaco enzyme, except that a 2.0 ml incubation volume was used. The total final volume was 7.0 ml. In assaying sweet potato enzyme, an Amylochrome tablet was dispersed in 2.0 ml of 0.001M $CaCl_2$, at 40° C, the enzyme added, incubated, and the reaction terminated with 2.2 ml of 2.6% or 5.0 ml of 1.8% trichloroacetic acid. Salivary amylase plus water to make 2.0 ml was incubated with an Amylochrome tablet at 37° C, and the enzyme activity terminated with 2.2 ml of acetate buffer, pH 3.5. As seen in Table 1, the tobacco enzyme released about 45 times more dye from the substrate of this invention than it did from the Amylochrome substrate. About 7 to 10 times greater response was obtained with 20 mg of the substrate of this invention than with 200 mg of Amylochrome substrate in reaction with salivary and sweet potato α-amylases (Table 2).

Using the substrate of this invention, duplicate assays agreed to ± 0.004 absorbance units when 20 mg of substrate was used and to ± 0.008 absorbance units when 70 mg of substrate was used. Dye units calculated for a sweet potato sample assayed using 70 mg substrate (0.234 dye units /Ml) and 20 mg substrate (0.247 dye untis /Ml) were similar and reaction rates were linear for at least 20 minutes.

The method using the new chromogenic substrate of this invention was also compared to the AOAC (Association of Official Agricultural Chemists) procedure. The AOAC (1970) method for α-amylase modified for use with sweet potatoes (J. Agr. Food Chem. 14, 237, 1966) was followed, except that a dextrin-iodine solution as described in J. Food Sci. 38, 338, 1973, was substituted for the comparator equipped with an α-amylase color disk. The results showed good correlation between the AOAC method and that of the substrate of this invention.

The great sensitivity of the substrate of this invention offers many advantages. Very dilute enzyme extracts can be analyzed which is important and advantageous especially when assaying extracts containing possible inhibitors. The highly sensitive nature of the substrate and process of this invention make it very advantageous for the analysis of plant α-amylases. This is especially so because there is no suitable substrate available as a general purpose tool for the analysis of plant α-amylases. In addition, it is certainly conceivable that the substrate and process of this invention has application for enzymes from other sources such as cereal α-amylases. Consequently, this invention is an important discovery and an extremely attractive addition to existing tools in the vast field of enzyme activity.

TABLE 1

Flue-cured tobacco α-amylase activity observed with Amylochrome[a] and with Improved substrate

| Substrate | mg Substrate | ml E[b] | Incubation time (min) | Absorbance (625 nm) | Units ml E 15 min |
|---|---|---|---|---|---|
| Amylochrome | 200 | 0.20 | 30 | 0.065 | 1 |
| Amylochrome | 200 | 0.40 | 30 | 0.113 | 0.8 |
| Amylochrome | 50 | 0.20 | 30 | 0.008 | 0.1 |
| Improved Substrate | 50 | 0.10 | 15 | 0.738[c] | 44.7 |

[a]The Amylochrome was washed with water and air dried prior to use.
[b]Enzyme extract.
[c]The amount of dyed amylose used was not sufficient for maximum activity at this level.

TABLE 2

Yam, Sweet Potato, and Human Salivary α-amylase activity obtained with Amylochrome tablets and with Improved substrate

| | | Amylochrome (200 mg substrate) | | | | Improved substrate (20 mg) | | | |
|---|---|---|---|---|---|---|---|---|---|
| | Sample | ml E[b] | E dil. | Absorbance (625 nm) | Units 1.0 ml juice or saliva | ml E[b] | E dil. | Absorbance (625 nm) | Units 1.0 ml juice or saliva |
| 1. | Yam | 0.30 | 1 → 100 | 0.024[a] | 30.0 | 0.10 | 1 → 100 | 0.118 | 461 |
| 2. | Yam | 0.40 | 1 → 100 | 0.063 | 56.0 | 0.10 | 1 → 100 | 0.170 | 671 |
| 3. | Sweet Potato | 0.10 | 1 → 25 | 0.116 | 104.5 | 0.10 | 1 → 250 | 0.101 | 995 |
| 4. | Human Saliva | 0.20 | 1 → 20,000 | 0.070 | 25,000 | 0.10 | 1 → 20,000 | 0.244 | 170,000 |
| 5. | Human Saliva | 0.20 | → 20,000 | 0.063 | 22,400 | 0.10 | → 20,000 | 0.211 | 147,000 |

[a]Since on reaction of sweet potato enzyme with Amylochrome, extrapolation to "zero" enzyme concentration gave an absorbance of about 0.03 units, a correction factor (0.03) was used for the sweet potato and yam results.
[b]Enzyme extract.

I claim:

1. In a process for preparing a chromogenic substrate product for the determination of amylase activity wherein amylose is reacted with Cibachron Blue F3GA, sodium sulfate and trisodium phosphate and the resulting dyed amylose substrate washed and dried, the steps for obtaining an improved highly sensitive substrate product having especial efficacy for determining α-amylase activity in plant and other very dilute enzyme extracts, comprising incubating the substrate obtained by the aforesaid reaction at about 44° C in a 0.04M phosphate buffer containing 0.001M calcium chloride, washing the incubated with water until practically colorless, and freeze-drying the washed product.

2. An improved chromogenic substrate for the determination of amylase activity comprising the product of the process of claim 1.

* * * * *